US008367366B2

(12) United States Patent
Tackett et al.

(10) Patent No.: US 8,367,366 B2
(45) Date of Patent: Feb. 5, 2013

(54) METHODS AND KITS FOR QUANTITATIVE METHYLTRANSFERASE AND DEMETHYLASE MEASUREMENTS

(75) Inventors: Alan J. Tackett, Little Rock, AR (US); Nathan L. Avaritt, Little Rock, AR (US); Lauren P. Blair, New Haven, CT (US)

(73) Assignee: The Board of Trustees of the University of Arkansas, Little Rock, AR (US)

( * ) Notice: Subject to any disclaimer, the term of this patent is extended or adjusted under 35 U.S.C. 154(b) by 128 days.

(21) Appl. No.: 12/960,486

(22) Filed: Dec. 4, 2010

(65) Prior Publication Data
US 2012/0142040 A1 Jun. 7, 2012

(51) Int. Cl.
*C12Q 1/26* (2006.01)
(52) U.S. Cl. ........................................................ 435/25
(58) Field of Classification Search ..................... 435/25
See application file for complete search history.

(56) References Cited

U.S. PATENT DOCUMENTS

| | | | |
|---|---|---|---|
| 7,670,795 | B2 | 3/2010 | Tackett et al. |
| 7,759,130 | B2 | 7/2010 | Oda et al. |
| 2003/0224473 | A1 | 12/2003 | McCafferty |
| 2004/0091951 | A1 | 5/2004 | Schultz |
| 2006/0111287 | A1 | 5/2006 | Bianchi |

OTHER PUBLICATIONS

Shi et al. Histone Demethylation Mediated by the Nuclear Amine Oxidase Homolog LSD1. Cell, vol. 119, 941-953.*
Geoghegan et al. Alternative Reducing Agents for Reductive Methylation of Amino Groups in Proteins. Int. J. Peptide Protein Res. 17, 1981, 345-352.*
Berger SL (2002) Histone modifications in transcriptional regulation. Curr Opin Genet Dev. 12(2):142-148.
Cheung WL, Briggs SD, Allis CD (2000) Acetylation and chromosomal functions. Curr Opin Cell Biol. Jun. 2000;12 (3):326-33.
Doyon, Y., W. Selleck, W.S. Lane, S. Tan and J. Cote (2004) Structural and functional conservation of the NuA4 histone acetyl transferase complex from yeast to humans. Mol. Cell. Biol. 24: 1884-1896.
Eberharter, A., S. John, P.A. Grant, R.T. Utley and J.L. Workman (1998) Identification and analysis of yeast nucleosomal histone acetyl transferase complexes. Methods 15: 315-321.
Espada J, Ballestar E, Fraga MF, Villar-Garea A, Juarranz A, Stocked JC, Robertson KD, Fuks F, Esteller M. (2004) Human DNA methyltransferase 1 is required for maintenance of the histone H3 modification pattern. J Biol Chem.279 (35):37175-84.
Glaser KB, Staver MJ, Waring JF, Stender J, Ulrich RG, Davidsen SK. (2003) Gene expression profiling of multiple histone deacetylase (HDAC) inhibitors: defining a common gene set produced by HDAC inhibition in T24 and MDA carcinoma cell lines. Mol Cancer Ther 2(2):151-163.
Grant, P.A., L. Duggan, J. Cote, S.M. Roberts, J.E. Brownell, R. Candau, R. Ohba, T. Owen-Hughes, C.D. Allis and F. Winston et al.
(1997) Yeast Gcn5 functions in two multisubunit complexes to acetylate nucleosomal histones: characterization of an Ada complex and the SAGA (Spt/Ada) complex. Genes Dev. 11: 1640-1650.
Hazzalin, C.A. and L.C. Mahadevan (2005) Dynamic acetylation of all lysine 4-methylated histone H3 in the mouse nucleus: analysis at c-fos and c-jun. PLoS Biol. 3: e393.
Howe, L., T. Kusch, N. Muster, R. Chaterji, J.R. Yates 3rd and J.L. Workman (2002) Ynglp modulates the activity of Sas3p as a component of the yeast NuA3 histone acetyl transferase complex. Mol. Cell. Biol. 22: 5047-5053.
Jenuwein and Allis, (2001) T. Jenuwein and C.D. Allis, Translating the histone code. Science 293: 1074-1080.
Kabani, M. Kabani, K. Michot, C. Boschiero and M. Werner (2005) Anc1 interacts with the catalytic subunits of the general transcription factors TFIID and TFIIF, the chromatin remodeling complexes RSC and INO80, and the histone acetyl transferase complex NuA3, Biochem. Biophys. Res. Commun. 332: 398-403.
Kimura A, Matsubara K, Horikoshi M. (2005) A decade of histone acetylation: marking eukaryotic chromosomes with specific codes. J Biochem (Tokyo). 138(6):647-62.
Lee KK, Workman JL. (2007) Histone acetyltransferase complexes: one size doesn't fit all. Nat Rev Mol Cell Biol. 8 (4):284-95.
Lorincz MC, Schübeler D, Groudine M. (2001) Methylation-mediated proviral silencing is associated with MeCP2 recruitment and localized histone H3 deacetylation. Mol Cell Biol. 21(23):7913-22.
Milne, T.A., Y. Dou, M.E. Martin, H.W. Brock, R.G. Roeder and J.L. Hess (2005) MLL associates specifically with a subset of transcriptionally active target genes. Proc. Natl. Acad. Sci. USA 102: 14765-14770.
Ng, HH, F. Robert, R.A. Young and K. Struhl (2003) Targeted recruitment of Set1 histone methylase by elongating Pol II provides a localized mark and memory of recent transcriptional activity. Mol. Cell 11:709-719.
Puig, O. et al. (2001) The tandem affinity purification (tap) method: a general procedure of protein complex purification. Methods 24, 218-229.
Rigaut, G. et al. (1999) A generic protein purification method for protein complex characterization and proteome exploration. Nat. Biotechnol. 17, 1030-1032.
Santos-Rosa, H, R. Schneider, A.J. Bannister, J. Sherriff, B.E. Bernstein, N.C. Emre, S.L. Schreiber, J. Mellor and T. Kouzarides (2002) Active genes are tri-methylated at K4 of histone H3. Nature 419: 407-411.
Schneider, R., A.J. Bannister, F.A. Myers, A.W. Thorne, C. Crane-Robinson and T. Kouzarides (2004) Histone H3 lysine 4 methylation patterns in higher eukaryotic genes. Nat. Cell Biol. 6: 73-77.
Sendra, R., C Tse and J.C. Hansen (2000) The yeast histone acetyltransferase A2 complex, but not free Gcn5p, binds stably to nucleosomal arrays. J. Biol. Chem. 275: 24928-24934.

(Continued)

*Primary Examiner* — Karen Cochrane Carlson
*Assistant Examiner* — Natalie Moss
(74) *Attorney, Agent, or Firm* — Hugh McTavish

(57) ABSTRACT

The invention provides methods and kits for characterizing the activity of a methyltransferase or demethylase. The method involves enzymatically methylating or demethylating in vitro a substrate that is a peptide fragment of a full-length polypeptide, and then non-enzymatically methylating the peptide substrate with methyl groups that differ in molecular weight from the enzymatically added or removed methyl groups. Typically, deuterated or $^{13}C$ formaldehyde is used to non-enzymatically methylate the substrate. The fully methylated substrate is then characterized by mass spectrometry to determine the ratio of enzymatically produced nonmethyl, monomethyl, and dimethyl residues on the peptide.

31 Claims, 7 Drawing Sheets

OTHER PUBLICATIONS

Smith CM, Gafken PR, Zhang Z, Gottschling DE, Smith JB, Smith DL. (2003) Mass spectrometric quantification of acetylation at specific lysines within the amino-terminal tail of histone H4. Anal Biochem. 316(1):23-33.

Strahl, B.D. and C.D. Allis (2000) The language of covalent histone modifications. Nature 403: 41-45.

Suzuki H, Gabrielson E, Chen W, Anbazhagan R, van Engeland M, Weijenberg MP, Herman JG, Baylin SB. (2002) A genomic screen for genes upregulated by demethylation and histone deacetylase inhibition in human colorectal cancer. Nat Genet 2002, 31(2):141-149.

Tacket, A.J. et al. (2005a) Proteomic and genomic characterization of chromatin complexes at a boundary. J. Cell Biol. 169:35-47.

Tacket, A.J. et al. (2005b) I-DIRT, a general method for distinguishing between specific and nonspecific protein interactions. J. Proteome Research 4:1752-1756.

Thiagalingam S, Cheng KH, Lee HJ, Mineva N, Thiagalingam A, Ponte JF. (2003) Histone deacetylases: unique players in shaping the epigenetic histone code. Ann N Y Acad Sci 983:84-100.

Workman, JL. (2006) Nucleosome displacement in transcription. Genes Devel. 20:2009-17.

Wysocka, J., T. Swigut, T.A. Milne, Y. Dou, X. Zhang, A.L. Burlingame, R.G. Roeder, A.H. Brivanlou and C.D. Allis (2005) WDR5 associates with histone H3 methylated at K4 and is essential for H3 K4 methylation and vertebrate development, Cell 121: 859-872.

Zhang, K. J.S. Siino, P.R. Jones, P.M. Yau and E.M. Bradbury (2004) A mass spectrometric "Western blot" to evaluate the correlations between histone methylation and histone acetylation, Proteomics 4: 3765-3775.

* cited by examiner

SEQUENCE LISTING

<160> NUMBER OF SEQ ID NOS: 2

<210> SEQ ID NO 1
<211> LENGTH: 21
<212> TYPE: PRT
<213> ORGANISM: Homo sapiens

<400> SEQUENCE: 1

Ala Arg Thr Lys Gln Thr Ala Arg Lys Ser Thr Gly Gly Lys Ala Pro

```
1               5                  10               15
Arg Lys Gln Leu Cys
               20

<210> SEQ ID NO 2
<211> LENGTH: 13
<212> TYPE: PRT
<213> ORGANISM: Homo sapiens

<400> SEQUENCE: 2

Ser Lys Ala Ala Arg Lys Ser Ala Pro Ser Thr Gly Gly
1               5                  10
```

METHODS AND KITS FOR QUANTITATIVE METHYLTRANSFERASE AND DEMETHYLASE MEASUREMENTS

GOVERNMENT SUPPORT

This invention was made with government support under grants P20RR015569, P20RR016460 and R01DA025755 awarded by the United States National Institutes of Health. The government has certain rights in the invention.

BACKGROUND

As a result of the sequencing of the human genome, it has become apparent that the complexity of an organism does not necessarily correlate with the size of its genome. This has sparked an interest in discovering exactly how genes are regulated on levels other than primary genomic sequence. Epigenetics has arisen as a field that addresses this concern by focusing on post-transcriptional methods of gene expression control including DNA methylation, histone post-translational modifications (PTMs) and non-coding RNAs (1). Modifications made to proteins post-translationally can affect their function, location or longevity. One set of highly modified proteins important to gene expression are histones. DNA is wrapped around histones, which form nucleosomes before being condensed into chromatin and ultimately chromosomes.

Histone PTMs have been shown to be very important to gene expression. Some modifications serve to signal the recruitment of chromatin modifying enzymes while some serve to alter the interaction between the histones and DNA allowing or prohibiting the access of transcription machinery (2). Some more common histone modifications include methylation, acetylation and phosphorylation. Of these common modifications, methylation is, by far, the most complex. Both lysine and arginine residues can be modified by mono- or di-methylation and lysine residues can be tri-methylated as well. These varying states of methylation can be associated with both active and inactive genes. The complexity and importance of methylation, on histones in particular, has stirred much interest in the enzymes capable of adding (methyltransferases) and removing (demethylases) these modifications.

The first demethylase was discovered in 2004 and was termed Lysine Specific Demethylase 1 or LSD1 (3). LSD1 is a flavin-dependent amine oxidase that can remove mono- and di-methyl marks from H3K4 primarily, H3K9 under certain conditions and some non-histone substrates such as p53 (4-6). It has been shown to be part of many protein complexes including CoREST, NuRD, and AR/ER (7). LSD1 is also associated with gene repression and has been suggested to be important in initiating myc-induced transcription in cancers (3, 8-11).

Structural and biochemical studies have led to the development of numerous LSD1 inactivators that have the potential to be therapeutic tools, much like the successful deacetylase inhibitors currently in use (12). In addition, the mechanism of LSD1 indicates that it is an excellent candidate for suicide inactivators. Many monoamine oxidase (MAO) inhibitors have been suggested as potential LSD1 suicide inactivators (13). Several different assays are used to study the activity of LSD1 in the presence and absence of these various inhibitors in order to determine their efficiency.

With the importance of histone methylation and demethylation in normal gene regulation and aberrant gene regulation in cancer and other diseases, improved tools to characterize the activity and specificity of enzymes catalyzing methylation and demethylation of histones and other proteins are needed.

SUMMARY

The invention involves methods and kit for characterizing the activity of a methylase or demethylase or enzyme mixture containing a methylase or demethylase. The methods involve enzymatically methylating and/or demethylating a peptide substrate that is a peptide fragment of a full-length polypeptide in vitro. Typically, this step adds or removes methyl groups of natural isotope distribution. After enzymatically methylating and/or demethylating the peptide substrate, the peptide substrate is chemically fully methylated with, e.g., deuterated formaldehyde and reductant. This results in a peptide with enzymatically added or removed methyl groups that have $^1H$ isotopic hydrogen and non-enzymatically added methyl groups that differ in molecular mass because they are deuterated. Mass spectrometry is then used to determine the masses of the product peptides, from which it can be determined how many of the methyl groups on the product peptide are deuterated and how many are not, and therefore whether the methyl groups were added (or removed) enzymatically, or were added by nonenzymatic methylation with deuterated methyl groups. Importantly, the method also allows one to quantitatively determine the ratio of nonmethyl, monomethyl, and dimethyl, and optionally trimethyl, species after enzymatic methylation or demethylation.

Other methods can determine whether a peptide or a particular residue on a peptide is methylated. But they cannot quantitatively determine the ratio of methylated species (nonmethylated, monomethyl, dimethyl, and optionally trimethyl residues) on a peptide or at a particular residue of the peptide. The present method can. This is because peptide species having nonmethyl, monomethyl, and dimethyl lysine residues, are different chemically, and thus in mass spectrometry can ionize with different efficiencies. But after fully methylating each species with a methyl reagent having normatural isotopic composition, the peptides are all fully methylated and are chemically identical. Thus, they ionize with equal efficiency. But they differ in their molecular weight depending on whether the peptide were nonmethylated, monomethylated, or dimethylated before being fully methylated nonenzymatically, and therefore they can be distinguished and quantitatively compared by mass spectrometry.

Applicants have developed a quantitative assay for differentiating between polypeptides having no methyl, monomethyl, and dimethyl groups on particular lysine residues and optionally trimethyl groups on lysine residues. The method studies enzymatic methylation or demethylation of a peptide, followed by non-enzymatic methylation, followed by mass spectrometry to differentiate between various lysine methylation states. This method accounts for methyl states within a sample, allowing sample-to-sample relative comparison. We have termed our assay MassSQUIRM (Mass Spectrometric Quantitation Using Isotopic Reductive Methylation).

In reductive methylation, lysine residues are chemically di-methylated using the following reactions to alkylate and then reduce amines:

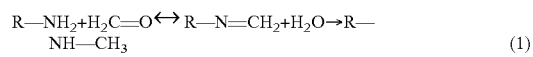

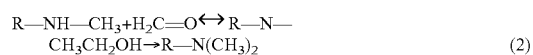

In the present method, we use a combination of methylation, isotopic labeling and mass spectrometry to quantitatively measure the activity of methylases or demethylases and the identity of lysine residues that are methylated or demethylated, and the number of methyl groups added or removed to each residue.

Thus, one embodiment provides a method for characterizing the activity of an enzyme or enzyme mixture comprising a methyltransferase or demethylase, the method comprising: first, (a) incubating the enzyme or enzyme mixture in vitro with a polypeptide substrate under conditions that allow methylation and/or demethylation of the polypeptide substrate to add methyl groups to or remove methyl groups from one or more lysine residues of the polypeptide substrate to generate an enzymatically methylated and/or demethylated polypeptide, wherein the polypeptide substrate is a peptide fragment of a full-length protein. The method, second, comprises (b) reacting the enzymatically methylated and/or demethylated polypeptide with one or more substances to non-enzymatically react with the polypeptide to add one or more methyl groups to the polypeptide to generate a fully dimethylated or trimethylated polypeptide that is fully dimethylated or trimethylated at least one lysine residue; wherein the methyl groups non-enzymatically added to the polypeptide differ in molecular weight from the added or removed methyl groups of the enzymatically methylated and/or demethylated protein or peptide. And the method, third, comprises (c) subjecting the fully methylated polypeptide to mass spectrometry to quantitatively determine a ratio of enzymatically produced nonmethyl, monomethyl, and dimethyl and optionally trimethyl lysine species at least one lysine residue.

Another embodiment of the invention provides a kit for characterizing the activity of a methyl transferase on a substrate, the kit comprising: (a) (i) a polypeptide substrate for a methyltransferase and/or demethylase, wherein the polypeptide substrate is a peptide fragment of a full-length protein or (ii) a methyltransferase or demethylase; and (b) a methylation reagent for nonenzymatic methylation selected from the group consisting of formaldehyde, iodomethane, and a reductant capable of reducing a Schiff base in vitro; and optionally (c) S-adenosyl methionine; wherein the methylation reagent or the polypeptide substrate have a non-natural isotopic composition, or if neither has a non-natural isotopic composition then S-adenosyl methionine is a component of the kit and has a non-natural isotopic composition.

DETAILED DESCRIPTION

Figure 1A:
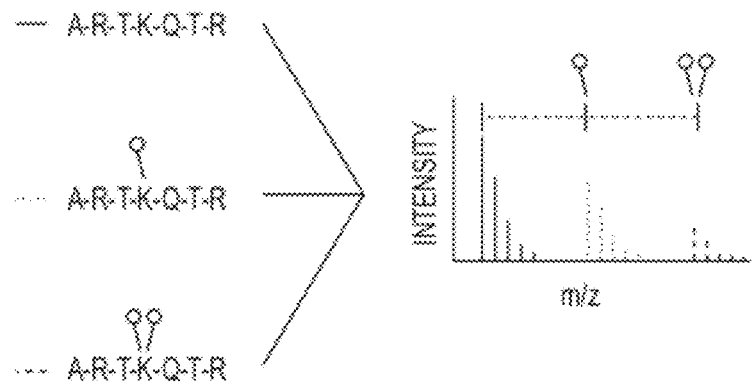
FIG. 1. Reductive methylation of histone H3. (A) The N-terminus of H3 is shown as being un- (solid line), mono- (dotted line), or di- (dashed line) methylated at lysine 4. On a MALDI mass spectrometer, addition of a single methyl group is recorded as an addition of 14 Da while addition of two methyl groups is recorded as an addition of 28 Da. Variation in the chemical composition of each peptide leads to differential ionization making quantification complex. (B) Reductive methylation converts all lysine residues to the di-methyl state which causes all peptides to be identical in mass and ionize similarly, however, it also makes the original methylation states indistinguishable. (C) The use of heavy formaldehyde in the reductive methylation reaction allows retention of the identity of the original methylation. In addition, all lysines are converted to the di-methyl state and will, thus, ionize similarly. Open circles indicate light methylation while closed circles indicate heavy methylation.

As an example of the method, a polypeptide substrate with a lysine residue, which is not methylated in the original substrate, is acted upon by a methylase with S-adenosyl methionine (SAM) having the normal natural isotopic composition as the methyl donor for the methylase. This results in addition of up to two methyl groups on a particular lysine residue. Some fraction of the substrate has one methyl group added, some none, and some two. Reductive methylation of the product peptide with deuterated formaldehyde donor after it is acted upon by the enzyme produces a peptide mixture where all peptides have the lysine residue dimethylated. But for the fraction that had no methyl groups after enzyme action, the methyl groups are "heavy" (deuterated), while for the fraction that was dimethylated by enzyme action both methyl groups are light, and for the fraction that was monomethylated by enzyme action, one methyl is light and one is heavy.

In one embodiment of the method, the mass spectrometry is MALDI mass spectrometry. MALDI does not fragment molecules; it just shows their molecular weight.

In many cases, it is known which residue on a peptide is acted upon by the enzyme, or the peptide has only one lysine or arginine residue and thus only one residue could be methylated. In these cases, MALDI provides all the information needed.

In other cases, it may be unknown which residue is methylated or two or more residues may be methylated and it may be desired to know the ratio of methylated species for each residue. In these cases, the residue methylated and the ratio of enzymatically produced nonmethyl, monomethyl, and dimethyl and optionally trimethyl species at each residue can be determined by tandem mass spectrometry. In this method, the polypeptide is fragmented in one step of the mass spectrometry, and the fragments are analyzed in a second step. Knowing the amino acid sequence of the polypeptide, from the masses of the fragments produced it is possible to identify the amino acid compositions of the fragments and which residue is methylated, as well as the ratio of enzymatically produced nonmethyl, monomethyl, and dimethyl, and optionally trimethyl species at each of the methylated residues.

Thus, one embodiment further comprises determining amino acid positions of enzymatically added or removed methyl groups on the polypeptide.

In another embodiment, the method comprises quantitatively determining a ratio of enzymatically produced nonmethyl, monomethyl, and dimethyl and optionally trimethyl lysine species at a first lysine residue identified by position and quantitatively determining a ratio of enzymatically produced nonmethyl, monomethyl, and dimethyl and optionally trimethyl lysine species at a second lysine residue identified by position.

In one embodiment of the methods, the mass spectrometry comprises MALDI mass spectrometry.

In another embodiment, the mass spectrometry comprises tandem mass spectrometry.

The substrate peptide can be methylated (prior to the tested enzymatic reaction) in some embodiments. This is necessary if enzymatic demethylation is studied. The methylation of the substrate may be at a different position than the position where enzymatic methylation and/or demethylation is to be studied, or it may be at the position that is to be enzymatically demethylated or further methylated.

In other embodiments, the polypeptide substrate is acetylated. For instance, lysine at the 7th position of a peptide may be acetylated and the enzymatic methylation of lysine at the 4th position may be studied.

In one embodiment, the enzyme or enzyme mixture comprises lysine specific demethylase 1 (LSD1).

In particular embodiments, the enzyme or enzyme mixture comprises a methyltransferase. In other embodiments, it comprises a demethylase.

Histones are key proteins whose methylation status affect gene regulation. In one embodiment, the polypeptide substrate is a polypeptide of a histone. In one embodiment, it is a polypeptide of histone H3.

In one embodiment, the polypeptide substrate comprises H3K4 or H3K9 (i.e., lysine 4 or lysine 9 of histone H3).

In one embodiment of the method, step (b) comprises reacting the enzymatically methylated and/or demethylated polypeptide with formaldehyde non-enzymatically to generate a formaldehyde-reacted polypeptide and reducing the formaldehyde reacted polypeptide to generate a fully dimethylated polypeptide.

In one embodiment of the method, step (a) comprises incubating the enzyme or enzyme mixture in vitro with two or more polypeptide substrates differing in their acetylation state but identical in their amino acid sequence, and the method comprises comparing activity of the enzyme or enzyme mixture on the two or more polypeptide substrates.

More generally, in one embodiment of the method, step (a) comprises incubating the enzyme or enzyme mixture in vitro with two or more polypeptide substrates differing in post-translational modifications but identical in their amino acid sequence, and the method comprises comparing activity of the enzyme or enzyme mixture on the two or more polypeptide substrates. The post-translational modifications may be, for example, acetylation or methylation. It may also be phosphorylation or glycosylation.

In particular embodiments where step (a) comprises incubating the enzyme or enzyme mixture in vitro with two or more polypeptide substrates differing in post-translational modifications but identical in their amino acid sequence, the two or more polypeptide substrates differ in methylation at one or more amino acid residues.

In particular embodiments, the polypeptide substrate comprises a synthetic ligand and the method further comprises before step (c) purifying the enzymatically acetylated and/or deacetylated polypeptide by contacting the polypeptide with a solid substrate coupled to a receptor for the ligand. For instance, the ligand may be biotin and the peptide may be purified by capturing it with avidin or streptavidin.

In a particular embodiment, the enzyme or enzyme mixture comprises a methyltransferase, and step (a) comprises incubating the methyltransferase in vitro with S-adenosyl methionine and the polypeptide substrate to generate an enzymatically methylated polypeptide.

In a particular embodiment, the enzyme or enzyme mixture comprises a demethylase, and step (a) comprises incubating the demethylase in vitro with a partially or fully methylated polypeptide substrate to generate an enzymatically demethylated polypeptide.

In one embodiment, the enzymatically added or removed methyl groups are of natural isotopic composition and the non-enzymatically added methyl groups contain at least one deuterium. In another embodiment, the enzymatically added or removed methyl groups are of natural isotopic composition and the non-enzymatically added methyl groups contain $^{13}C$.

In a particular embodiment, the polypeptide substrate is enzymatically methylated and/or demethylated on two or more amino acid residues.

One embodiment of the invention provides a kit for characterizing the activity of a methyl transferase on a substrate, the kit comprising: (a) (i) a polypeptide substrate for a methyltransferase and/or demethylase, wherein the polypeptide substrate is a peptide fragment of a full-length protein or (ii) a methyltransferase or demethylase; and (b) a methylation reagent for nonenzymatic methylation selected from the group consisting of formaldehyde, iodomethane, and a reductant capable of reducing a Schiff base in vitro; and optionally (c) S-adenosyl methionine; wherein the methylation reagent or the polypeptide substrate have a non-natural isotopic composition, or if neither has a non-natural isotopic composition then S-adenosyl methionine is a component of the kit and has a non-natural isotopic composition.

The kit may also have both an enzyme and a polypeptide substrate, i.e., it may comprise (a) (i) a polypeptide substrate for a methyltransferase and/or demethylase, wherein the polypeptide substrate is a peptide fragment of a full-length protein and (ii) a methyltransferase or demethylase.

In specific embodiments, the kit comprises a polypeptide substrate.

In specific embodiments, the kit comprises a methyltransferase or demethylase.

In one embodiment, the kit comprises $d_2$-formaldehyde.

In one embodiment, the polypeptide substrate comprises a synthetic ligand. In a more specific embodiment, the kit further comprises a solid substrate coupled to a receptor for the ligand.

In one embodiment, the kit contains two or more polypeptide substrates that differ in post-translational modifications but are identical in their amino acid sequence.

In a particular embodiment, the kit comprises S-adenosyl methionine.

In a particular embodiment, the polypeptide substrate is a substrate for methylation and/or demethylation by the methyltransferase and/or demethylase at two or more amino acid residues.

In one embodiment the kit comprises a polypeptide substrate for a methyltransferase and/or demethylase, wherein the polypeptide substrate is a peptide fragment of a full-length protein. In one embodiment the kit comprises a methyltransferase or demethylase;

The invention will now be illustrated by the following examples.

EXAMPLE 1

Reductive Dimethylation of Lysine Residues

Materials and Methods

MassSQUIRM Lysine residues were chemically dimethylated using a reductive methylation technique adapted from Rayment, et al (21). Briefly, 5 µg of synthetic histone H3 peptide ([1]ARTKQTARKSTGGKAPRKQLC (SEQ ID NO:1)) (the superscript 1 refers to the alanine residue being the first residue of the H3 protein) was resuspended in 50 mM sodium phosphate pH 7.4 then 0.12 mg of borane dimethylamine (Sigma) and 3.2 mM isotopically light formaldehyde (Sigma) or isotopically heavy $d_2$-formaldehyde (Cambridge Isotope Laboratories) were sequentially added. This reaction was incubated for 2 hours at 4° C. Fresh aliquots of borane dimethylamine and formaldehyde were added and the reaction was again incubated at 4° C. for two hours. A final aliquot of borane dimethylamine was added and the reaction was incubated at 4° C. for ~16 hours. The reaction was quenched with 80 mM Tris-Cl, pH 7.5. Peptides were incubated with POROS R2 20 micron beads (Applied Biosystems), collected with a $C_{18}$ ZipTip™ (Millipore) and spotted for MALDI analysis in 2,5-dihydroxybenzoic acid. Mass spectra of peptides were collected with a MALDI-prOTOF mass spectrometer (PerkinElmerSciex) (61, 62). Spectra were viewed and peak areas extracted using MoverZ™ software (Genomic Solutions). Reaction products were verified by $MS^2$ with a Thermo LTQ XL mass spectrometer coupled to a NanoLC-2D™ liquid chromatography system (Eksigent). Un-, mono- and dimethylated K27 versions of synthetic histone H3 peptide ([22]SKAARKSAPSTGG (SEQ ID NO:2)) were used for dynamic range experiments.

Demethylase Assay. The demethylase reaction consisted of 0.25 µg H3K4me2-biotin peptide ([1]ARTKme2QTARKSTGGKAPRKQLYKbiotin) plus 15.6, 31.3, 62.5, 125, 250 or 500 ng recombinant LSD1 (BPS Biosciences) in the following reaction buffer: 50 mM Tris-Cl pH 8.5, 50 mM KCl, 5 mM $MgCl_2$, 5% glycerol. The reaction proceeded for 2 hr at 37° C. Reaction products were collected with POROS R2 20 micron beads for 15 minutes at room temperature, loaded into a $C_{18}$ ZipTip, eluted in 40 µL 70% acetonitrile/0.1% TFA, lyophilized, and subjected to MassSQUIRM as described above.

LSD1 Inhibition Assay. Inhibition experiments were performed in triplicate under demethylase assay conditions as described above using 0.25 µg of H3K4me2-bio peptide alone, peptide with 125 ng GST-LSD1 (prepared in-house), and peptide with LSD1 and 16.7 mM phenylethylhydrazine inhibitor (Chem Services). As described above, peptides were isolated with POROS R220 micron beads and ZipTips prior to Mass SQUIRM analysis.

Results

Reductive Methylation is an Efficient Method for Modifying Lysine Residues. We chose to use reductive methylation to address the issue of differential ionization of methylated peptides. Ordinarily, methylation is seen in mass spectrometric data as an addition of 14 Da with mono-methylation (one open circle, FIG. 1A) and 28 Da with di-methylation (two open circles, FIG. 1A). It might seem logical to compare the peak areas of the three monoisotopic peaks seen in FIG. 1A in order to quantify their abundance. This would lead us to believe that the unmethylated peptide (corresponding to the solid line monoisotopic peak) is in higher abundance than the mono-methylated (dotted line) and di-methylated (dashed line) peptides. This, however, is not necessarily a correct assumption. It is possible that the unmethylated peptide is differentially ionized as compared to the others and is thus recorded by the mass spectrometer detector at a higher level. For this reason, we cannot compare these three peaks in a quantitative manner.

Figure 1B:
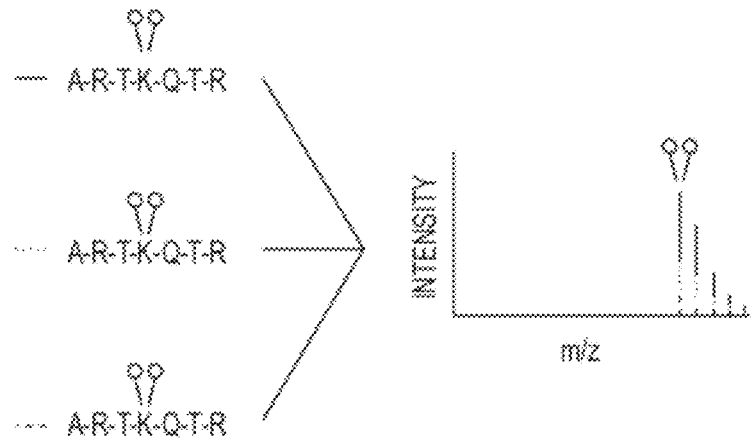

Reductive methylation is a reaction involving formaldehyde that results in dimethylated lysine residues. Using this technique, we can convert all three peptides in FIG. 1 to the same chemical species and thus cause them to ionize identically (FIG. 1B). Unfortunately, this causes them to all be contained in a single monoisotopic peak, from which we cannot decipher the original methylation state of each individual peptide.

Figure 1C:
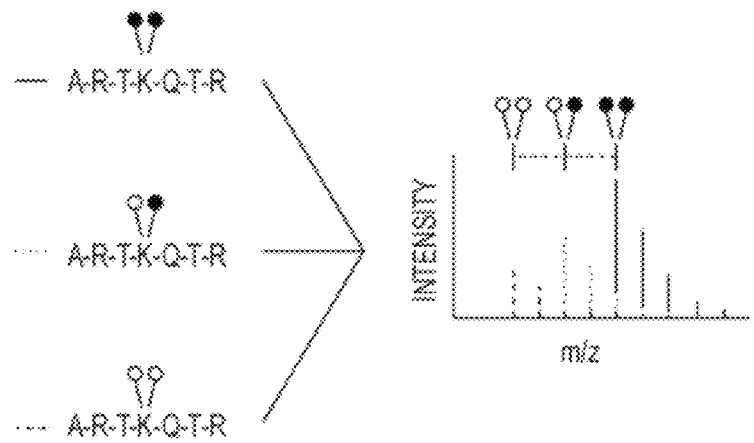

To solve this dilemma, we chose to use deuterated formaldehyde in our reactions. Reductive methylation performed with heavy formaldehyde results in the addition of up to two deuterated methyl groups to lysine residues and the N-terminus. Pre-existing methyl lysines will be isotopically light (open circles), while methyl groups added by reductive methylation will be isotopically heavy (closed circles) (FIG. 1C). Peptides with dimethylated lysines will be separated by 2 or 4 Da, depending on the number of deuterated methyl groups added, but will ionize identically (FIG. 1C). Once peptides are converted to the dimethylation state by reductive methylation, we can compare their peak areas in a quantitative manner.

Figure 2A:
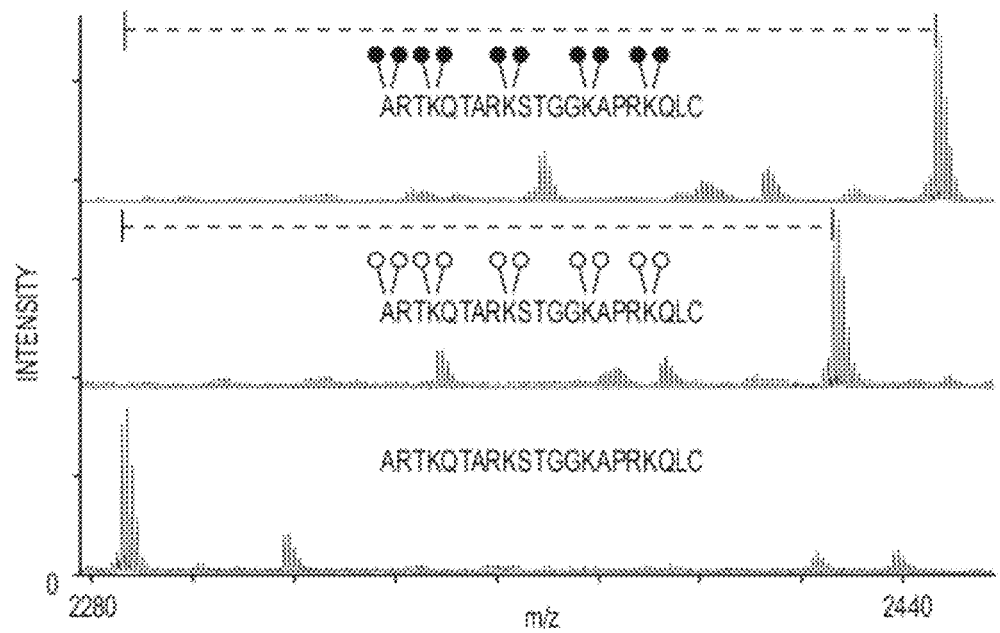
FIG. 2. Efficiency and dynamic range of MassSQUIRM. (A) A synthetic peptide containing four unmodified lysine residues (lower panel) was exposed to reductive methylation using either light formaldehyde (middle panel) or heavy formaldehyde (top panel). The resulting spectra show a ~100% conversion of all lysine residues, as well as the N-terminus, to the di-methyl state. Heavy formaldehyde showed a peak 20 Da larger than that of the light formaldehyde as would be expected. (B) Equimolar amounts of an H3K27 peptide with 0, 1 or 2 methyl groups were mixed and analyzed by MALDI mass spectrometry. The un-, mono- and di-methylated peptides ionize at different efficiencies. (C) Un-, mono- and di-methylated synthetic peptides were normalized to a 1:1:1 mixture and mono-methylated peptide concentration was varied at the ratios indicated. (D) The same synthetic peptides were mixed in ratios indicated in (C) and treated using MassSQUIRM. (E) The linear dynamic range of MassSQUIRM was determined to be 1:8 for both treated (♦) and untreated (■) samples. Observed ratios were determined by compensating for isotopic overlap found in 1:1 unmodified monomethyl species. Open circles indicate light methylation while closed circles indicate heavy methylation.

To determine the efficiency of the reductive methylation reaction using both heavy and light formaldehyde, we subjected a synthetic peptide, containing four unmodified lysine residues, to both forms of the reaction. We found that the reaction is ~100% efficient when using light or heavy formaldehyde (FIG. 2A). Reductive methylation also occurs on the N-terminus of the peptide as is shown in FIG. 2A. We observed an addition of ten methyl groups to the peptide (two for each lysine and two on the N-terminal residue) totaling 140 Da with light formaldehyde and 160 Da with heavy formaldehyde.

Figure 2B:
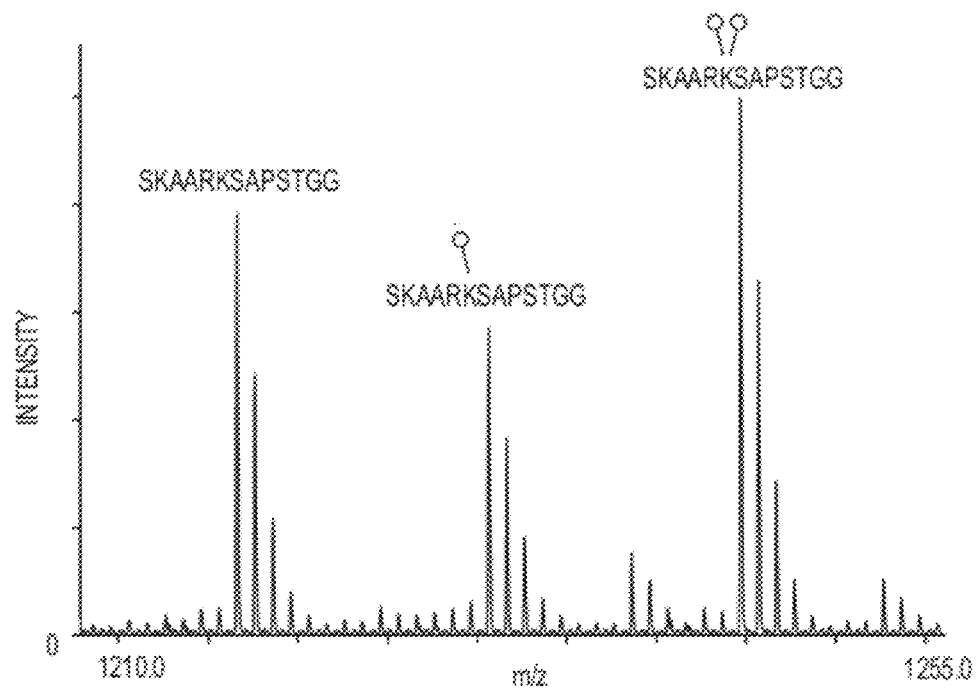
Figure 2C:
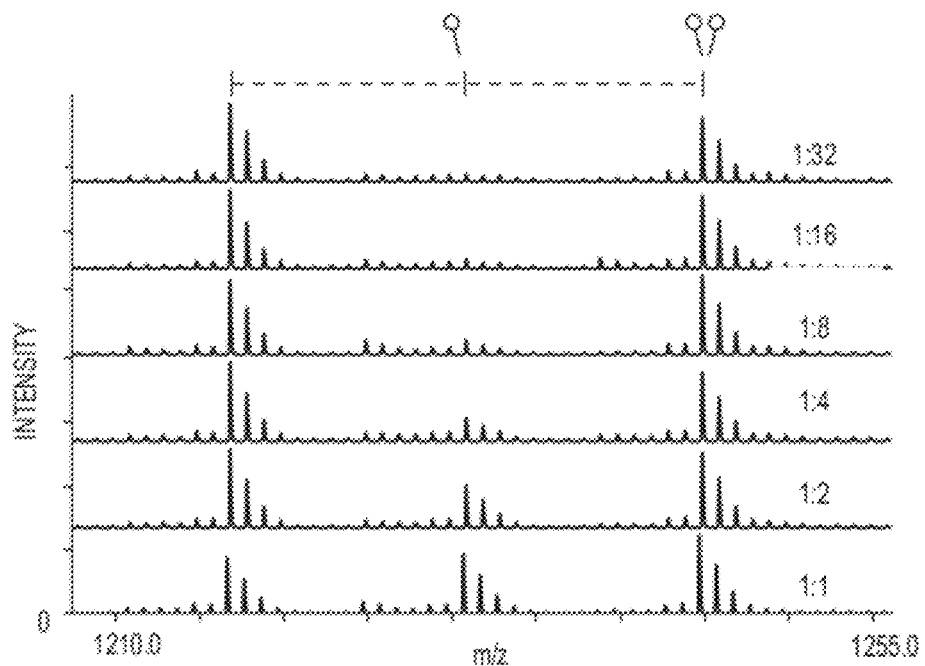
Figure 2D:
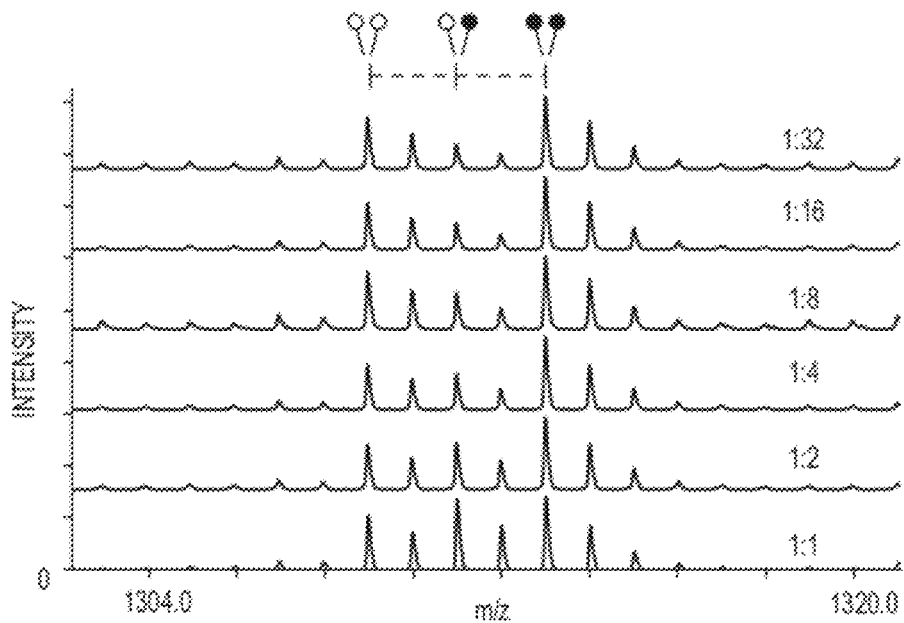
Figure 2E:
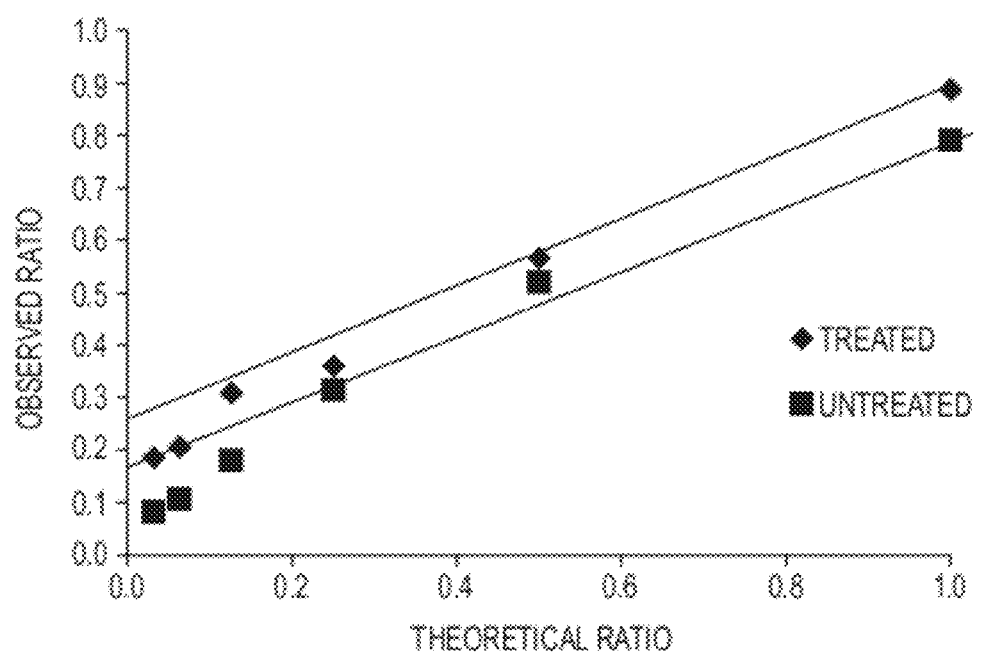

It is prudent to take into consideration the dynamic range capabilities of both your experiment and the instrument which will be used for analysis because a linear response is needed for accurate quantification. To determine the dynamic range of our assay, we used three different forms of a synthetic peptide: un-, mono-, and di-methylated. When the peptides were added at equal amounts, the mass spectrum showed nonequivalent levels of peptide ionization—illustrating that modified peptides do not necessarily ionize equally (FIG. 2B). To study the dynamic range, the amount of each peptide added to produce a mass spectrum with equivalent peptide ionization was empirically determined (FIG. 2C, 1:1 spectrum). The un- and di-methylated peptides were mixed at a ratio of 1:1. The mono-methylated peptide was mixed with the others at the following ratios: 1:1, 1:2, 1:4, 1:8, 1:16 and 1:32 (FIG. 2C). The observed ratio was determined by diving the monoisotopic areas under the mono-methyl peak by the un- and di-methylated peaks. Using this method, we determined a dynamic range of 1:8 (FIG. 2E, squares). To check the dynamic range following reductive methylation chemistry, we incubated the same peptides in the same ratios but exposed them to MassSQUIRM analysis (FIG. 2D). We determined the peak ratios as mentioned above with added compensation for isotopic overlap as described in the next section. We determined the dynamic range following reductive methylation to be 1:8 as well (FIG. 2E, diamonds).

Figure 3A:
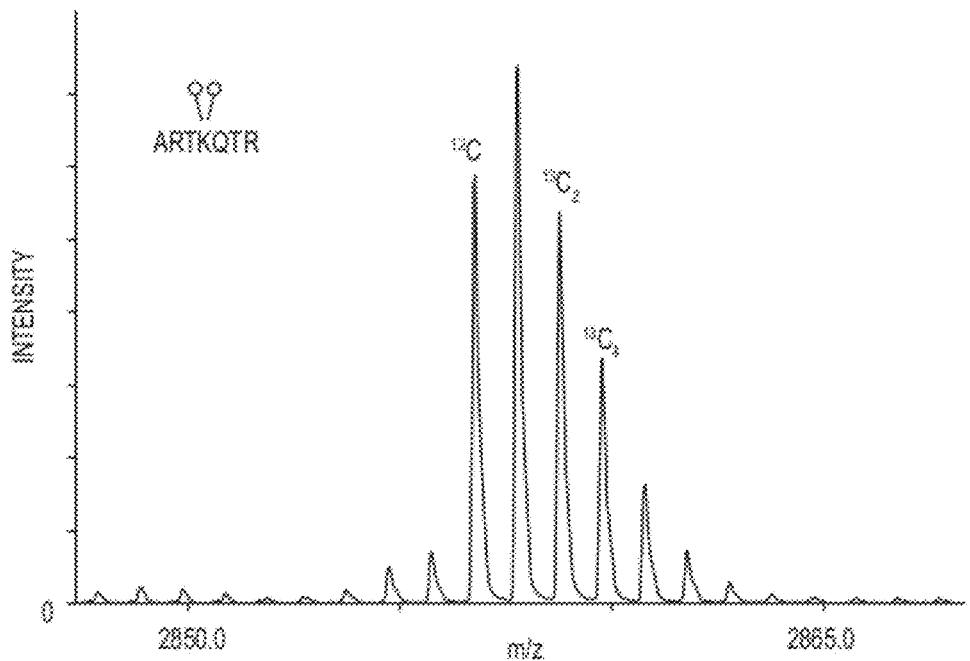
FIG. 3. MassSQUIRM can be used to successfully quantify differentially modified peptides. (A) A dimethylated synthetic peptide was analyzed using mass spectrometry and peak ratios relative to the monoisotopic peak were noted as $r_1$ and $r_2$ in equations 3 and 4. (B) The same synthetic peptide was incubated with 125 ng GST-LSD1 in demethylase buffer for two hours at 37° C. Samples were then subjected to MassSQUIRM analysis. A mixed population of overlapping peaks represents three different methylation states as seen in FIG. 1C. Areas under the monoisotopic peaks were noted as $A_1$, $A_2$, and $A_3$. These values were used to determine equations 5-7. Open circles indicate light methylation while closed circles indicate heavy methylation.

Development of a Method for Compensating for Isotopic Overlap when Using MassSQUIRM. When using mass spectrometry for relative quantification, it is most common to compare the lowest mass, or monoisotopic, peak between peptides. In addition to the monoisotopic peak, a given peptide will show a series of peaks representing naturally occurring isotopes, which are termed the isotopic envelope. When two peptides are similar in mass and are being relatively compared, the isotopic envelopes can overlap and complicate quantification. As can be seen in FIG. 1C, one caveat with the use of deuterated formaldehyde in reductive methylation is that some isotopic overlap occurs between the different peptides. For example, the second monoisotopic peak in FIG. 1C (1 open and 1 closed circle) contains some overlap from the isotopic envelope of the first peptide (2 open circles). In order to compensate for this overlap, we first determined the peak area (A) ratio of $^{13}C_2$ and $^{13}C_4$ isotopes relative to the monoisotopic peak for the peptide with light dimethylation (FIG. 3A).

$$A_{13C2}/A_{12C} = r_1 \quad (3)$$

$$A_{13C4}/A_{12C} = r_2 \quad (4)$$

This gave us the ratio of peptide existing in these isotopic states ($r_1$ & $r_2$) specific to our experiment and mass spectrometer. We then used this information to determine the following formulas for quantifying the amount of peptide existing in each modification state in a sample:

$$H3K4me2 = A_1 \quad (5)$$

$$H3K4me = A_2 - r_1(A_1) \quad (6)$$

$$H3K4 = A_3 - r_2(A_1) - [r_1(A_2 - r_1(A_1))] \quad (7)$$

Figure 3B:
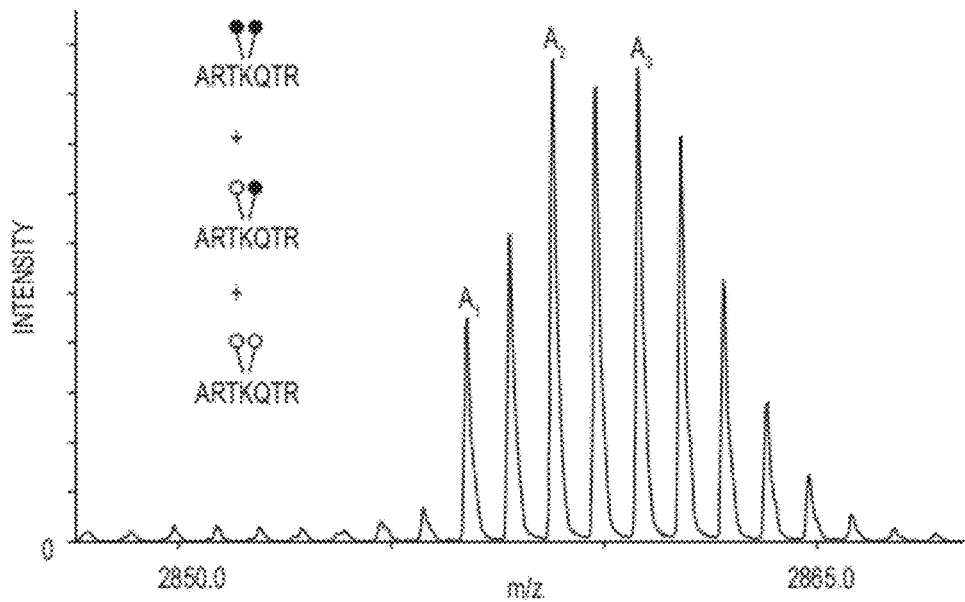

As an example, we have shown an LSD1 treated H3K4 peptide following heavy reductive methylation (0.25 μg LSD1+0.25 μg H3K4me2 from FIG. 4a) that exists in multiple states of methylation (FIG. 3B). This method was used to generate all quantitative data presented in this paper.

Figure 4A:
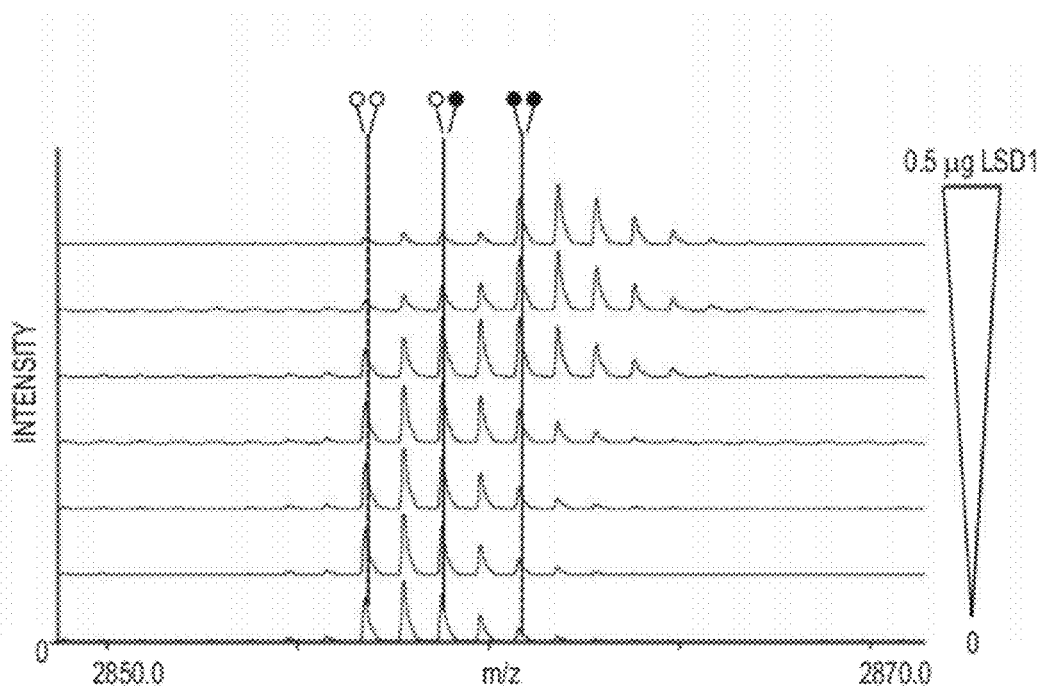
FIG. 4. LSD1 activity can be measured using MassSQUIRM. (A) 0.25 μg of a synthetic H3K4me2 peptide was subjected to varying concentrations of recombinant LSD1 in demethylase buffer for two hours at 37° C. and analyzed with MassSQUIRM. (B) Quantification of methylation levels was determined using $r_1$ and $r_2$ values from peptide alone samples (bottom panel) and equations 5-7 below. Open circles indicate light methylation while closed circles indicate heavy methylation.
Figure 4B:
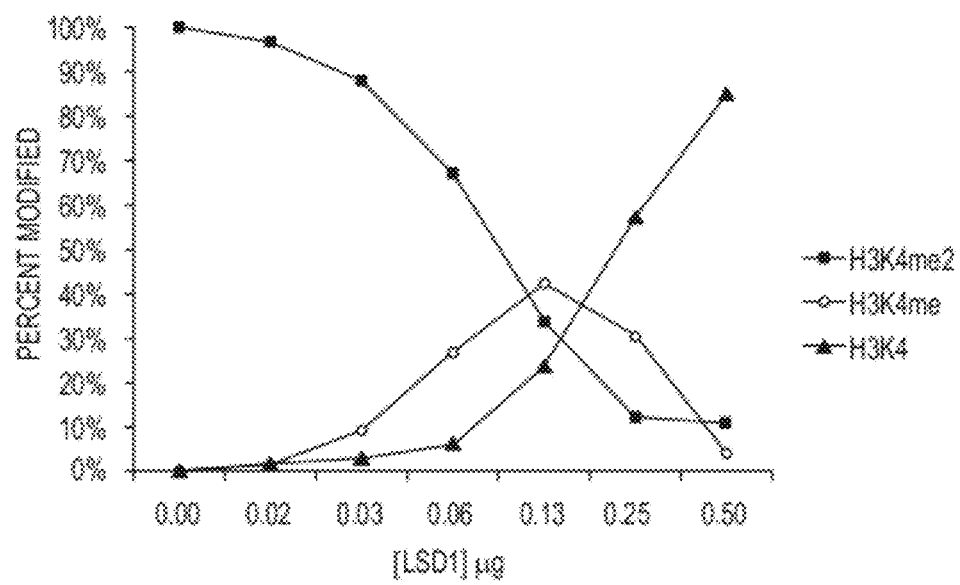

LSD1 Activity can be Quantitatively Measured Using MassSQUIRM. Once we had optimized the heavy reductive methylation reaction, we decided to use it to determine the activity of a demethylase. Even though LSD1 has been extensively studied, a reliable method for quantitatively studying its demethylase activity has proven elusive. For this reason, we chose to use LSD1 to test the ability of MassSQUIRM as a method for determining demethylase activity in vitro. Histone demethylase assays were performed using a synthetic H3K4me2 peptide and varying concentrations of LSD1. Samples were then subjected to MassSQUIRM (FIG. 4A). The resulting mass spectra showed an increase in LSD1 activity as LSD1 concentration was increased from zero to 0.5 μg. A shift of peptide methylation state from completely di-methylated to 97% un-methylated was observed when using 0.5 μg LSD1 (FIG. 4B). These results indicate that MassSQUIRM is an appropriate method for measuring the activity of LSD1 by quantitatively following methylation levels in vitro.

Figure 5A:
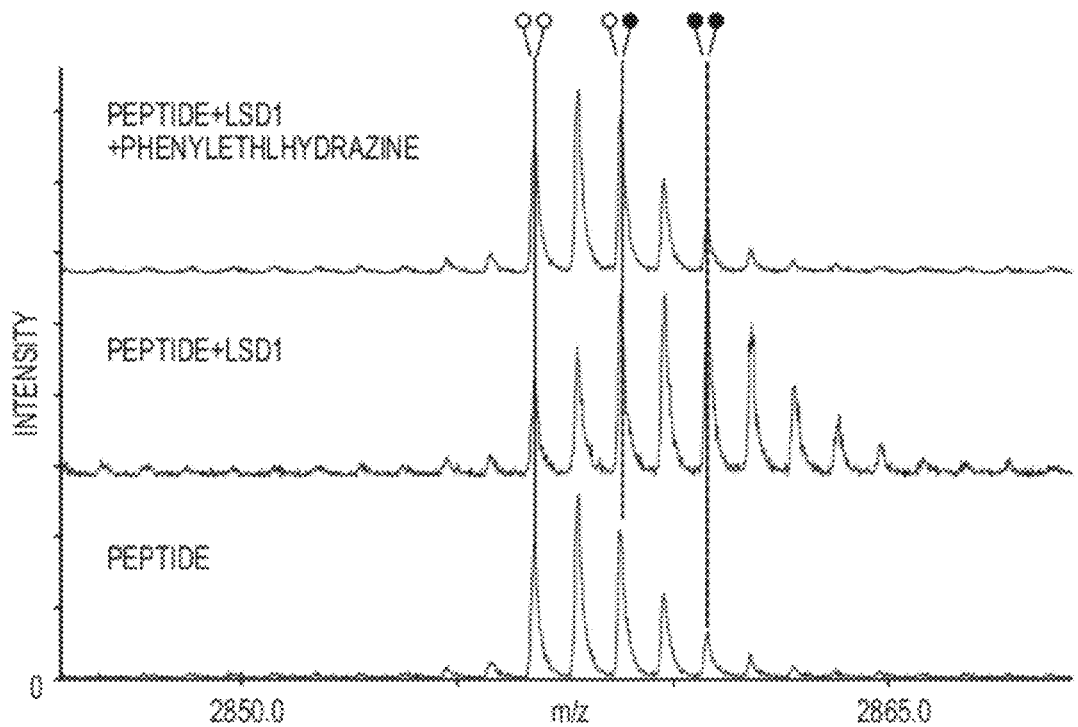
FIG. 5. LSD1 inhibitor efficiency can be measured quantitatively using MassSQUIRM. (A) Demethylation reactions were carried out using 125 ng of LSD1 and 0.25 μg H3K4me2 peptide in the presence (top panel) or absence (middle panel) of 16.7 mM of the LSD1 inhibitor phenylethylhydrazine. (B) Quantification of methylation levels was determined using $r_1$ and $r_2$ values from peptide alone samples (A, bottom panel) and equations 5-7. Open circles indicate light methylation while closed circles indicate heavy methylation.
Figure 5B:
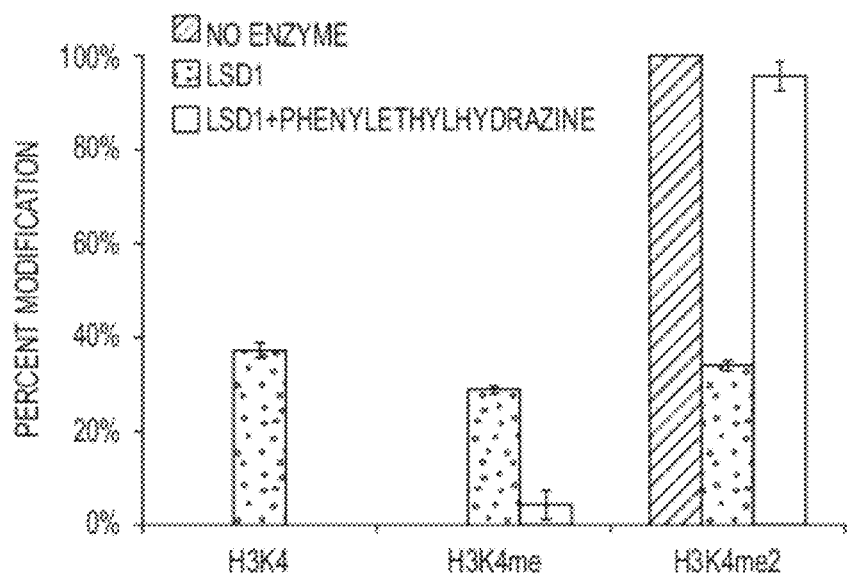

To emphasize the importance of our assay, we repeated the above experiment using phenylethylhydrazine, an MAO inhibitor known to inhibit LSD1 activity. We chose to use 0.125 μg LSD1 for this assay because it yielded a mixed population of modifications in our initial experiments (FIG. 4). Triplicate samples of peptide alone, peptide with LSD1 and peptide with LSD1 with phenylethylhydrazine were subjected to histone demethylation assays. Following these assays, samples were analyzed by MassSQUIRM. Upon addition of LSD1, we observed a shift of spectra to greater mass, indicating a mixed population of methylation states (FIG. 5A, middle relative to bottom panel). When samples were treated with LSD1 and its inhibitor, the shift disappeared (FIG. 5A, top panel) indicating inhibition of LSD1 activity. Samples containing peptide alone (FIG. 5A, bottom panel) were used to determine the experimental $r_1$ and $r_2$ values used to quantify the results. Under these conditions, phenylethylhydrazine inhibits LSD1 activity by 96% (FIG. 5B).

Discussion

The recent discovery of lysine demethylases has led to an overwhelming amount of correspondences in a very short amount of time (22-38).

Currently, demethylase activity can only be measured semi-quantitatively by methods such as autoradiography, formaldehyde release and western blotting. Mass spectrometry, as shown here, can provide an excellent method for attaining quantitative measurements of post-translational modifications. Because lysine methylation can occur in three different states, it is possible to have four different populations (un-, mono-, di- and tri-) in a single sample. Deciphering, quantifying and comparing these different methyl states can be challenging. An assay with the ability to follow each of these different methyl states quantitatively within a population does not currently exist. Most currently available mass spectrometric methods used to quantify changes in PTM status of a peptide are complex and expensive (39). In this work, we present a straightforward and inexpensive mass spectrometry-based method for quantifying the activity of demethylases acting on mono- and di-methyl lysines.

Since the initial discovery of LSD1, more than twenty human demethylase enzymes have been identified (7). Several efforts to classify these enzymes in detail are currently underway. Many demethylases have already been implicated as potential cancer diagnostic and prognostic indicators while some have been implicated as potential targets for therapies (40). Since, most histone demethylase mechanisms involve redox chemistry, they are prime candidates for suicide inactivators (13). We have shown that phenylethylhydrazine, an MAO inhibitor, serves to inhibit LSD1 activity by 96% (FIG. 5B). Further studies of this inactivator could lead to its use in inhibiting LSD1 in some cancers. Our assay can be used to further classify the effect of this drug on different diseases involving LSD1, possibly leading to rapid turnaround for therapeutic use.

We chose to test our assay on LSD1, specifically, due to the existence of a wealth of literature suggesting that it is important in many diseases and the availability of a number of LSD1 inhibitors (3, 12, 41-45). Overexpression of LSD1 in prostate cancer, poorly differentiated neuroblastoma and estrogen receptor (ER)-negative breast cancer has been associated with aggressive forms of these diseases (5, 40, 46, 47). There have also been some promising results indicating that LSD1 inhibitors, in combination with other drugs, lead to slower growth of colon cancer in mouse xenograft models (48). All signs point to LSD1 being an excellent target for drug development.

LSD1 exists as a component of several complexes, many of which contain histone deacetylase enzymes (28, 49-51). Deacetylase inhibitors have been used successfully in clinical trials and could be used in combination with demethylase inhibitors to provide potent treatment for some diseases (52). Interestingly, when LSD1 interacts with androgen receptor, its specificity changes from H3K4 to H3K9 although this interaction has not been verified in vitro (5). Current assays exist that allow the study of interactions between LSD1 and its associating proteins, yet these assays merely represent a qualitative measure of the effect of these interactions on LSD1 activity. When studying protein complexes, it is common to combine interacting proteins in vitro and perform enzymatic assays to try and reconstruct the optimal complex. These results are used to design inhibitors that may affect a component of a complex that is not necessarily the ultimate target but that would have the same biological effect (53). For this reason, our assay will be useful in designing new drugs to target diseases that involve LSD1 and its various complexes.

Although LSD1 is the most commonly studied demethylase enzyme to date, there are several other demethylases that have not been as well characterized. Some have already been shown to be important factors in human disease (40). Members of the JMJD1 family of lysine demethylases remove mono- and di-methyl marks from H3K9 resulting in removal of a repressive mark (54). Thus, these enzymes are most likely associated with activating genes but limited analysis of them has been performed. More extensive studies of these enzymes will be undertaken before more definite conclusions can be made about their role in human disease.

We present MassSQUIRM as an inexpensive and quantitative method for comprehensive study of the activity of demethylases involved in mono- and di-methylation. MassSQUIRM offers quantitation not only of the product of the reactions of these enzymes but also their intermediates. This assay will be a powerful tool in studying the mechanism of LSD1 and possibly its interacting partners. It will also serve as a useful tool in classifying many newly discovered lysine demethylase enzymes such as PHF8 and could be used for certain methyltransferase enzymes (25, 27, 55-60). MassSQUIRM is the first assay of its kind to offer a quantitative method for studying LSD1 activity, thus its impact on the field has the potential to be quite extensive.

EXAMPLE 2

Nonenzmymatic Trimethylation of Lysine

Example 1 shows nonenzymatic methylation of lysine residues to dimethyl lysine. Some lysine residues are biologically trimethylated. In order to quantitatively compare trimethyl lysines to monomethyl, dimethyl, and unmethylated lysines, it is necessary to nonenzymatically methylate lysines all the way to trimethyl lysine. The formaldehyde method does not do this. A stronger methylation method is needed. In this example, iodomethane is used to nonenzymatically trimethylate lysine residues. As is described above, with this nonenzymatic methylation reaction, one can quantitatively compare the extent of enzymatic methylation or demethylation by enzymatically methylating or demethylating a peptide, and then nonenzymatically methylating the peptide to trimethyl lysines, where the nonenzymatically added methyl groups differ in molecular weight (isotopic composition) from the enzymatically added or removed methyl groups.

The lysine trimethylation reaction was modified from a method described by Stewart et al (63). Briefly, 50 µg of histone H3 peptide (Abcam), amino acids 23-34, was lyophilized in 4×40 mm glass reaction vessels (made in house from glass tubing). This vessel was placed in a 10 mm×7 inch glass NMR tube (Fisher Scientific) and a narrow constriction was formed near the top of the tube with a Bunsen burner. The lower portion of this tube was submerged in liquid nitrogen and the tube was evacuated with a vacuum pump. Nitrogen gas was introduced to the NMR tube and was evacuated. This process was repeated three times to remove any water vapor or oxygen in the NMR tube. Next, 100 uL of iodomethane (Sigma) was added to lyophilized peptide while streaming nitrogen gas across the top of the NMR tube. The tube was evacuated again and sealed under vacuum at the constriction point. The NMR tube containing reaction vessels were placed in a dry block heater and incubated for 15 hours at 75° C. The next day the NMR tube was broken and the reaction vessel was removed. Peptides were dissolved in 150 µL of 2% triethylamine and transferred to a 1.5 mL microcentrifuge tube. This tube was placed in a dry block heater for 1 hour at 90° C. then lyophilized. Peptides are analyzed by mass spectrometry to quantify un-, mono-, di- and trimethylation levels on lysines.

REFERENCES

1. Goldberg, A. D., Allis, C. D., and Bernstein, E. (2007) Epigenetics: a landscape takes shape, *Cell* 128, 635-638.
2. Kouzarides, T. (2007) Chromatin modifications and their function, *Cell* 128, 693-705.
3. Shi, Y., Lan, F., Matson, C., Mulligan, P., Whetstine, J. R., Cole, P. A., and Casero, R. A. (2004) Histone demethylation mediated by the nuclear amine oxidase homolog LSD1, *Cell* 119, 941-953.
4. Formeris, F., Binda, C., Vanoni, M. A., Battaglioli, E., and Mattevi, A. (2005) Human histone demethylase LSD1 reads the histone code, *J Biol Chem* 280, 41360-41365.
5. Metzger, E., Wissmann, M., Yin, N., Muller, J. M., Schneider, R., Peters, A. H., Gunther, T., Buettner, R., and Schule, R. (2005) LSD1 demethylates repressive histone marks to promote androgen-receptor-dependent transcription, *Nature* 437, 436-439.
6. Nicholson, T. B., and Chen, T. (2009) LSD1 demethylates histone and non-histone proteins, *Epigenetics* 4, 129-132.
7. Mosammaparast, N., and Shi, Y. Reversal of histone methylation: biochemical and molecular mechanisms of histone demethylases, *Annu Rev Biochem* 79, 155-179.
8. Amente, S., Bertoni, A., Morano, A., Lania, L., Avvedimento, E. V., and Majello, B. LSD1-mediated demethylation of histone H3 lysine 4 triggers Myc-induced transcription, *Oncogene* 29, 3691-3702.
9. Lakowski, B., Roelens, I., and Jacob, S. (2006) CoREST-like complexes regulate chromatin modification and neuronal gene expression, *J Mol Neurosci* 29, 227-239.
10. Shi, Y. J., Matson, C., Lan, F., Iwase, S., Baba, T., and Shi, Y. (2005) Regulation of LSD1 histone demethylase activity by its associated factors, *Mol Cell* 19, 857-864.

11. Lim, S., Metzger, E., Schule, R., Kirfel, J., and Buettner, R. Epigenetic regulation of cancer growth by histone demethylases, *Int J Cancer*.
12. Culhane, J. C., and Cole, P. A. (2007) LSD1 and the chemistry of histone demethylation, *Curr Opin Chem Biol* 11, 561-568.
13. Cole, P. A. (2008) Chemical probes for histone-modifying enzymes, *Nat Chem Biol* 4, 590-597.
14. Chellappan, S. P. (2009) *Chromatin protocols,* 2nd ed., Humana Press, New York, N.Y.
15. Yamane, K., Tateishi, K., Klose, R. J., Fang, J., Fabrizio, L. A., Erdjument-Bromage, H., Taylor-Papadimitriou, J., Tempst, P., and Zhang, Y. (2007) PLU-1 is an H3K4 demethylase involved in transcriptional repression and breast cancer cell proliferation, *Mol Cell* 25, 801-812.
16. Bordeaux, J., Welsh, A., Agarwal, S., Killiam, E., Baquero, M., Hanna, J., Anagnostou, V., and Rimm, D. Antibody validation, *Biotechniques* 48, 197-209.
17. Connor, C., Cheung, I., Simon, A., Jakovcevski, M., Weng, Z., and Akbarian, S. A simple method for improving the specificity of anti-methyl histone antibodies, *Epigenetics* 5.
18. Cloos, P. A., Christensen, J., Agger, K., Maiolica, A., Rappsilber, J., Antal, T., Hansen, K. H., and Helin, K. (2006) The putative oncogene GASC1 demethylates tri- and dimethylated lysine 9 on histone H3, *Nature* 442, 307-311.
19. Smith, C. M., Gafken, P. R., Zhang, Z., Gottschling, D. E., Smith, J. B., and Smith, D. L. (2003) Mass spectrometric quantification of acetylation at specific lysines within the amino-terminal tail of histone H4, *Anal Biochem* 316, 23-33.
20. Tackett, A. J., Dilworth, D. J., Davey, M. J., O'Donnell, M., Aitchison, J. D., Rout, M. P., and Chait, B. T. (2005) Proteomic and genomic characterization of chromatin complexes at a boundary, *J Cell Biol* 169, 35-47.
21. Rayment, I., Rypniewski, W. R., Schmidt-Base, K., Smith, R., Tomchick, D. R., Benning, M. M., Winkelmann, D. A., Wesenberg, G., and Holden, H. M. (1993) Three-dimensional structure of myosin subfragment-1: a molecular motor, *Science* 261, 50-58.
22. Ciccone, D. N., Su, H., Hevi, S., Gay, F., Lei, H., Bajko, J., Xu, G., Li, E., and Chen, T. (2009) KDM1B is a histone H3K4 demethylase required to establish maternal genomic imprints, *Nature* 461, 415-418.
23. Greer, E. L., Maures, T. J., Hauswirth, A. G., Green, E. M., Leeman, D. S., Maro, G. S., Han, S., Banko, M. R., Gozani, O., and Brunet, A. Members of the H3K4 trimethylation complex regulate lifespan in a germline-dependent manner in *C. elegans*, *Nature*.
24. Katz, D. J., Edwards, T. M., Reinke, V., and Kelly, W. G. (2009) A *C. elegans* LSD1 demethylase contributes to germline immortality by reprogramming epigenetic memory, *Cell* 137, 308-320.
25. Liu, W., Tanasa, B., Tyurina, O. V., Zhou, T. Y., Gassmann, R., Liu, W. T., Ohgi, K. A., Benner, C., Garcia-Bassets, I., Aggarwal, A. K., Desai, A., Dorrestein, P. C., Glass, C. K., and Rosenfeld, M. G. PHF8 mediates histone H4 lysine 20 demethylation events involved in cell cycle progression, *Nature*.
26. Metzger, E., Imhof, A., Patel, D., Kahl, P., Hoffmeyer, K., Friedrichs, N., Muller, J. M., Greschik, H., Kirfel, J., Ji, S., Kunowska, N., Beisenherz-Huss, C., Gunther, T., Buettner, R., and Schule, R. Phosphorylation of histone H3T6 by PKCbeta(I) controls demethylation at histone H3K4, *Nature* 464, 792-796.
27. Qi, H. H., Sarkissian, M., Hu, G. Q., Wang, Z., Bhattacharjee, A., Gordon, D. B., Gonzales, M., Lan, F., Ongusaha, P. P., Huarte, M., Yaghi, N. K., Lim, H., Garcia, B. A., Brizuela, L., Zhao, K., Roberts, T. M., and Shi, Y. Histone H4K20/H3K9 demethylase PHF8 regulates zebrafish brain and craniofacial development, *Nature* 466, 503-507.
28. Wang, Y., Zhang, H., Chen, Y., Sun, Y., Yang, F., Yu, W., Liang, J., Sun, L., Yang, X., Shi, L., Li, R., Li, Y., Zhang, Y., Li, Q., Yi, X., and Shang, Y. (2009) LSD1 is a subunit of the NuRD complex and targets the metastasis programs in breast cancer, *Cell* 138, 660-672.
29. Lan, F., Bayliss, P. E., Rinn, J. L., Whetstine, J. R., Wang, J. K., Chen, S., Iwase, S., Alpatov, R., Issaeva, I., Canaani, E., Roberts, T. M., Chang, H. Y., and Shi, Y. (2007) A histone H3 lysine 27 demethylase regulates animal posterior development, *Nature* 449, 689-694.
30. Li, F., Huarte, M., Zaratiegui, M., Vaughn, M. W., Shi, Y., Martienssen, R., and Cande, W. Z. (2008) Lid2 is required for coordinating H3K4 and H3K9 methylation of heterochromatin and euchromatin, *Cell* 135, 272-283.
31. Okada, Y., Scott, G., Ray, M. K., Mishina, Y., and Zhang, Y. (2007) Histone demethylase JHDM2A is critical for Tnp1 and Prm1 transcription and spermatogenesis, *Nature* 450, 119-123.
32. Perillo, B., Ombra, M. N., Bertoni, A., Cuozzo, C., Sacchetti, S., Sasso, A., Chiariotti, L., Malorni, A., Abbondanza, C., and Avvedimento, E. V. (2008) DNA oxidation as triggered by H3K9me2 demethylation drives estrogen-induced gene expression, *Science* 319, 202-206.
33. Tateishi, K., Okada, Y., Kallin, E. M., and Zhang, Y. (2009) Role of Jhdm2a in regulating metabolic gene expression and obesity resistance, *Nature* 458, 757-761.
34. De Santa, F., Totaro, M. G., Prosperini, E., Notarbartolo, S., Testa, G., and Natoli, G. (2007) The histone H3 lysine-27 demethylase Jmjd3 links inflammation to inhibition of polycomb-mediated gene silencing, *Cell* 130, 1083-1094.
35. Huang, J., Sengupta, R., Espejo, A. B., Lee, M. G., Dorsey, J. A., Richter, M., Opravil, S., Shiekhattar, R., Bedford, M. T., Jenuwein, T., and Berger, S. L. (2007) p53 is regulated by the lysine demethylase LSD1, *Nature* 449, 105-108.
36. Lan, F., Collins, R. E., De Cegli, R., Alpatov, R., Horton, J. R., Shi, X., Gozani, O., Cheng, X., and Shi, Y. (2007) Recognition of unmethylated histone H3 lysine 4 links BHC80 to LSD1-mediated gene repression, *Nature* 448, 718-722.
37. Lee, M. G., VIIIa, R., Trojer, P., Norman, J., Yan, K. P., Reinberg, D., Di Croce, L., and Shiekhattar, R. (2007) Demethylation of H3K27 regulates polycomb recruitment and H2A ubiquitination, *Science* 318, 447-450.
38. Tahiliani, M., Mei, P., Fang, R., Leonor, T., Rutenberg, M., Shimizu, F., Li, J., Rao, A., and Shi, Y. (2007) The histone H3K4 demethylase SMCX links REST target genes to X-linked mental retardation, *Nature* 447, 601-605.
39. Schulze, W. X., and Usadel, B. Quantitation in mass-spectrometry-based proteomics, *Annu Rev Plant Biol* 61, 491-516.
40. Lim, S., Janzer, A., Becker, A., Zimmer, A., Schule, R., Buettner, R., and Kirfel, J. Lysine-specific demethylase 1 (LSD1) is highly expressed in ER-negative breast cancers and a biomarker predicting aggressive biology, *Carcinogenesis* 31, 512-520.
41. Culhane, J. C., Wang, D., Yen, P. M., and Cole, P. A. Comparative analysis of small molecules and histone substrate analogues as LSD1 lysine demethylase inhibitors, *J Am Chem Soc* 132, 3164-3176.

42. Yang, M., Culhane, J. C., Szewczuk, L. M., Jalili, P., Ball, H. L., Machius, M., Cole, P. A., and Yu, H. (2007) Structural basis for the inhibition of the LSD1 histone demethylase by the antidepressant trans-2-phenylcyclopropylamine, *Biochemistry* 46, 8058-8065.

43. Yang, M., Culhane, J. C., Szewczuk, L. M., Gocke, C. B., Brautigam, C. A., Tomchick, D. R., Machius, M., Cole, P. A., and Yu, H. (2007) Structural basis of histone demethylation by LSD1 revealed by suicide inactivation, *Nat Struct Mol Biol* 14, 535-539.

44. Szewczuk, L. M., Culhane, J. C., Yang, M., Majumdar, A., Yu, H., and Cole, P. A. (2007) Mechanistic analysis of a suicide inactivator of histone demethylase LSD1, *Biochemistry* 46, 6892-6902.

45. Culhane, J. C., Szewczuk, L. M., Liu, X., Da, G., Marmorstein, R., and Cole, P. A. (2006) A mechanism-based inactivator for histone demethylase LSD1, *J Am Chem Soc* 128, 4536-4537.

46. Kahl, P., Gullotti, L., Heukamp, L. C., Wolf, S., Friedrichs, N., Vorreuther, R., Solleder, G., Bastian, P. J., Ellinger, J., Metzger, E., Schule, R., and Buettner, R. (2006) Androgen receptor coactivators lysine-specific histone demethylase 1 and four and a half LIM domain protein 2 predict risk of prostate cancer recurrence, *Cancer Res* 66, 11341-11347.

47. Schulte, J. H., Lim, S., Schramm, A., Friedrichs, N., Koster, J., Versteeg, R., Ora, I., Pajtler, K., Klein-Hitpass, L., Kuhfittig-Kulle, S., Metzger, E., Schule, R., Eggert, A., Buettner, R., and Kirfel, J. (2009) Lysine-specific demethylase 1 is strongly expressed in poorly differentiated neuroblastoma: implications for therapy, *Cancer Res* 69, 2065-2071.

48. Huang, Y., Stewart, T. M., Wu, Y., Baylin, S. B., Marton, L. J., Perkins, B., Jones, R. J., Woster, P. M., and Casero, R. A., Jr. (2009) Novel oligoamine analogues inhibit lysine-specific demethylase 1 and induce reexpression of epigenetically silenced genes, *Clin Cancer Res* 15, 7217-7228.

49. Wang, J., Scully, K., Zhu, X., Cai, L., Zhang, J., Prefontaine, G. G., Krones, A., Ohgi, K. A., Zhu, P., Garcia-Bassets, I., Liu, F., Taylor, H., Lozach, J., Jayes, F. L., Korach, K. S., Glass, C. K., Fu, X. D., and Rosenfeld, M. G. (2007) Opposing LSD1 complexes function in developmental gene activation and repression programmes, *Nature* 446, 882-887.

50. Lee, M. G., Norman, J., Shilatifard, A., and Shiekhattar, R. (2007) Physical and functional association of a trimethyl H3K4 demethylase and Ring6a/MBLR, a polycomb-like protein, *Cell* 128, 877-887.

51. Lee, M. G., Wynder, C., Cooch, N., and Shiekhattar, R. (2005) An essential role for CoREST in nucleosomal histone 3 lysine 4 demethylation, *Nature* 437, 432-435.

52. Beumer, J. H., and Tawbi, H. Role of Histone Deacetylases and Their Inhibitors in Cancer Biology and Treatment, *Curr Clin Pharmacol*.

53. Mayers, M., Ruderman, E. M., and Perlman, H. (2009) Intracellular signal pathways: potential for therapies, *Curr Rheumatol Rep* 11, 378-385.

54. Yamane, K., Toumazou, C., Tsukada, Y., Erdjument-Bromage, H., Tempst, P., Wong, J., and Zhang, Y. (2006) JHDM2A, a JmjC-containing H3K9 demethylase, facilitates transcription activation by androgen receptor, *Cell* 125, 483-495.

55. Fortschegger, K., de Graaf, P., Outchkourov, N. S., van Schaik, F. M., Timmers, H. T., and Shiekhattar, R. PHF8 targets histone methylation and RNA polymerase II to activate transcription, *Mol Cell Biol* 30, 3286-3298.

56. Loenarz, C., Ge, W., Coleman, M. L., Rose, N. R., Cooper, C. D., Klose, R. J., Ratcliffe, P. J., and Schofield, C. J. PHF8, a gene associated with cleft lip/palate and mental retardation, encodes for an Nepsilon-dimethyl lysine demethylase, *Hum Mol Genet* 19, 217-222.

57. Suganuma, T., and Workman, J. L. Features of the PHF8/KIAA1718 histone demethylase, *Cell Res*.

58. Yu, L., Wang, Y., Huang, S., Wang, J., Deng, Z., Zhang, Q., Wu, W., Zhang, X., Liu, Z., Gong, W., and Chen, Z. Structural insights into a novel histone demethylase PHF8, *Cell Res* 20, 166-173.

59. Yue, W. W., Hozjan, V., Ge, W., Loenarz, C., Cooper, C. D., Schofield, C. J., Kavanagh, K. L., Oppermann, U., and McDonough, M. A. Crystal structure of the PHF8 Jumonji domain, an Nepsilon-methyl lysine demethylase, *FEBS Lett* 584, 825-830.

60. Zhu, Z., Wang, Y., Li, X., Xu, L., Wang, X., Sun, T., Dong, X., Chen, L., Mao, H., Yu, Y., Li, J., Chen, P. A., and Chen, C. D. PHF8 is a histone H3K9me2 demethylase regulating rRNA synthesis, *Cell Res* 20, 794-801.

61. Collom, S. L., Jamakhandi, A. P., Tackett, A. J., Radominska-Pandya, A., and Miller, G. P. (2007) CYP2E1 active site residues in substrate recognition sequence 5 identified by photoaffinity labeling and homology modeling, *Arch Biochem Biophys* 459, 59-69.

62. Gradolatto, A., Rogers, R. S., Lavender, H., Taverna, S. D., Allis, C. D., Aitchison, J. D., and Tackett, A. J. (2008) *Saccharomyces cerevisiae* Yta7 Regulates Histone Gene Expression, *Genetics* 179, 291-304.

63. Stewart N A, Pham V T, Choma C T, Kaplan H. (2002) Improved peptide detection with matrix-assisted laser desorption/ionization mass spectrometry by trimethylation of amino groups, *Rapid Commun. Mass Spectrom.* 16: 1448-1453.

All patents, patent documents, and other references cited are hereby incorporated by reference.

What is claimed is:

1. A method for characterizing the activity of an enzyme or enzyme mixture comprising a methylase or demethylase, the method comprising:
   (a) incubating the enzyme or enzyme mixture in vitro with a polypeptide substrate under conditions that allow methylation and/or demethylation of the polypeptide substrate to add methyl groups to or remove methyl groups from one or more lysine residues of the polypeptide substrate to generate an enzymatically methylated and/or demethylated polypeptide, wherein the polypeptide substrate is a peptide fragment of a full-length protein;
   (b) reacting the enzymatically methylated and/or demethylated polypeptide with one or more substances to non-enzymatically react with the polypeptide to add one or more methyl groups to the polypeptide to generate a fully dimethylated or trimethylated polypeptide that is fully dimethylated or trimethylated at least one lysine residue; wherein the methyl groups non-enzymatically added to the polypeptide differ in molecular weight from the added or removed methyl groups of the enzymatically methylated and/or demethylated protein or peptide; and
   (c) subjecting the fully methylated polypeptide to mass spectrometry to quantitatively determine a ratio of enzymatically produced nonmethyl, monomethyl, and dimethyl and optionally trimethyl lysine species at least one lysine residue.

2. The method of claim 1 further comprising determining amino acid positions of enzymatically added or removed methyl groups on the polypeptide.

3. The method of claim 2 wherein the method comprises quantitatively determining a ratio of enzymatically produced nonmethyl, monomethyl, and dimethyl and optionally trimethyl lysine species at a first lysine residue identified by position and quantitatively determining a ratio of enzymatically produced nonmethyl, monomethyl, and dimethyl and optionally trimethyl lysine species at a second lysine residue identified by position.

4. The method of claim 2 wherein the mass spectrometry is tandem mass spectrometry.

5. The method of claim 1 wherein the mass spectrometry comprises MALDI mass spectrometry.

6. The method of claim 1 wherein the polypeptide substrate is methylated.

7. The method of claim 1 wherein the polypeptide substrate is acetylated.

8. The method of claim 1 wherein the enzyme or enzyme mixture comprises lysine specific demethylase 1 (LSD1).

9. The method of claim 1 wherein the polypeptide substrate is a polypeptide of histone H3.

10. The method of claim 9 wherein the polypeptide substrate comprises H3K4 or H3K9.

11. The method of claim 1 wherein step (b) comprises reacting the enzymatically methylated and/or demethylated polypeptide with formaldehyde non-enzymatically to generate a formaldehyde-reacted polypeptide and reducing the formaldehyde reacted polypeptide to generate a fully dimethylated polypeptide.

12. The method of claim 1 wherein step (a) comprises incubating the enzyme or enzyme mixture in vitro with two or more polypeptide substrates differing in post-translational modifications but identical in their amino acid sequence, and the method comprises comparing activity of the enzyme or enzyme mixture on the two or more polypeptide substrates.

13. The method of claim 12 wherein the two or more polypeptide substrates differ in methylation at one or more amino acid residues.

14. The method of claim 1 wherein the polypeptide substrate comprises a synthetic ligand and the method further comprises before step (c) purifying the enzymatically acetylated and/or deacetylated polypeptide by contacting the polypeptide with a solid substrate coupled to a receptor for the ligand.

15. The method of claim 1 wherein the enzyme or enzyme mixture comprises a methyltransferase, and step (a) comprises incubating the methyltransferase in vitro with S-adenosyl methionine and the polypeptide substrate to generate an enzymatically methylated polypeptide.

16. The method of claim 1 wherein the enzyme or enzyme mixture comprises a demethylase, and step (a) comprises incubating the demethylase in vitro with a partially or fully methylated polypeptide substrate to generate an enzymatically demethylated polypeptide.

17. The method of claim 1 wherein the enzymatically added or removed methyl groups are of natural isotopic composition and the non-enzymatically added methyl groups contain at least one deuterium.

18. The method of claim 1 wherein the polypeptide substrate is a peptide fragment of a histone.

19. The method of claim 1 wherein the polypeptide substrate is enzymatically methylated and/or demethylated on two or more amino acid residues.

20. The method of claim 2 wherein the polypeptide substrate is enzymatically methylated and/or demethylated on two or more amino acid residues.

21. A kit for characterizing the activity of a methyltransferase or demethylase on a substrate, the kit comprising:

(a) (i) a polypeptide substrate for a methyltransferase and/or demethylase, wherein the polypeptide substrate is a peptide fragment of a full-length protein or (ii) a methyltransferase or demethylase; and (b) a methylation reagent for nonenzymatic methylation selected from the group consisting of formaldehyde, iodomethane, and a reductant capable of reducing a Schiff base in vitro; and optionally (c) S-adenosyl methionine;

wherein the methylation reagent or the polypeptide substrate have a non-natural isotopic composition, or if neither has a non-natural isotopic composition then S-adenosyl methionine is a component of the kit and has a non-natural isotopic composition.

22. The kit of claim 21 wherein the polypeptide substrate is a fragment of a full-length histone.

23. The kit of claim 21 wherein the kit comprises $d_2$-formaldehyde or $^{13}C$-formaldehyde.

24. The kit of claim 21 wherein the polypeptide substrate comprises a synthetic ligand and the kit further comprises a solid substrate coupled to a receptor for the ligand.

25. The kit of claim 21 wherein the polypeptide substrate is methylated.

26. The kit of claim 21 wherein the polypeptide substrate is acetylated.

27. The kit of claim 21 wherein the kit contains two or more polypeptide substrates that differ in post-translational modifications but are identical in their amino acid sequence.

28. The kit of claim 21 wherein the kit comprises S-adenosyl methionine.

29. The kit of claim 21 wherein the polypeptide substrate is a substrate for methylation and/or demethylation by the methyltransferase and/or demethylase at two or more amino acid residues.

30. The kit of claim 22 wherein the polypeptide substrate is a peptide fragment of histone H3 and comprises H3K4 or H3K9.

31. The kit of claim 21 wherein the kit comprises:
(a) (i) a polypeptide substrate for a methyltransferase and/or demethylase, wherein the polypeptide substrate is a peptide fragment of a full-length protein and (ii) a methyltransferase or demethylase.

* * * * *